(12) United States Patent
Akaike et al.

(10) Patent No.: US 6,372,194 B1
(45) Date of Patent: Apr. 16, 2002

(54) MRI CONTRAST MEDIA RECOGNIZING MINOR ENVIRONMENTAL CHANGES

(75) Inventors: Toshihiro Akaike, 4-15-23, Shimohouya, Houya-shi, Tokyo 202-0004; Masahito Mikawa, Machida; Atsushi Maruyama, Yokohama; Naoto Miwa, Takatsuki, all of (JP)

(73) Assignees: Toshihiro Akaike, Tokyo; Nihon Schering K.K., Osaka, both of (JP)

( * ) Notice: Subject to any disclaimer, the term of this patent is extended or adjusted under 35 U.S.C. 154(b) by 0 days.

(21) Appl. No.: 09/381,176
(22) PCT Filed: Mar. 16, 1998
(86) PCT No.: PCT/JP98/01099
§ 371 Date: Sep. 17, 1999
§ 102(e) Date: Sep. 17, 1999
(87) PCT Pub. No.: WO98/41241
PCT Pub. Date: Sep. 24, 1998

(30) Foreign Application Priority Data

Mar. 18, 1997 (JP) ............................................. 9-064497

(51) Int. Cl.[7] ................................................ A61B 5/055
(52) U.S. Cl. .................. 424/9.323; 424/9.3; 424/9.322; 424/9.1; 424/1.11
(58) Field of Search ............................... 424/1.11, 1.65, 424/9.1, 9.3, 9.322, 9.323; 206/223, 569, 570; 534/7, 10–16; 128/654, 653.2

(56) References Cited

U.S. PATENT DOCUMENTS

| 4,822,594 A | * | 4/1989 | Gibby | 424/9.1 |
|---|---|---|---|---|
| 5,446,145 A | | 8/1995 | Love et al. | 540/465 |
| 5,494,655 A | | 2/1996 | Rocklage et al. | 424/9.36 |
| 5,681,543 A | | 10/1997 | Schmitt-Willich et al. | 424/934 |
| 5,681,544 A | | 10/1997 | Schmitt-Willich et al. | 424/9.34 |
| 5,980,862 A | * | 11/1999 | Meade et al. | 424/9.35 |

FOREIGN PATENT DOCUMENTS

| EP | 0 331 616 | 9/1989 |
|---|---|---|
| JP | 5-214096 | 8/1993 |
| JP | 5-506793 | 10/1993 |

OTHER PUBLICATIONS

R. Moats et al., "A 'Smart' Magnetic Resonance Imaging Agent That Reports on Specific Enzymatic Activity", Int. Ed. Engl. 36, No. 7, pp. 726–728, (1987).

* cited by examiner

Primary Examiner—Dameron L. Jones
(74) Attorney, Agent, or Firm—Wenderoth, Lind & Ponack, L.L.P.

(57) ABSTRACT

This relates to a contrast medium containing a complex of a gadolinium (Gd) type contrast agent and a polymer. More particularly, the contrast medium wherein the polymer capable of phase transit in response to environmental changes, particularly, pH, light or temperature, to develop a different water solubility, and a method for imaging by the use of this contrast medium. By binding a polymer responsive to microenvironmental changes with a Gd type MRI contrast agent, on-off switching of MRI imaging capability is enabled, wherein imaging occurs only on the target sites. Consequently, a highly specific MRI contrast medium can be obtained, whereby a highly specific MRI diagnosis is made possible, wherein only the target sites such as a tumor and a particular site are imaged and otherwise at the site where imaging is not necessary.

35 Claims, 12 Drawing Sheets

MRI CONTRAST MEDIA RECOGNIZING MINOR ENVIRONMENTAL CHANGES

This application is a 371 of PCT/JP98/01099, filed on Mar. 16, 1998.

TECHNICAL FIELD

The present invention relates to contrast media comprising a complex of gadolinium (Gd) type contrast agent and a polymer. More particularly, the present invention relates to such contrast media wherein the polymer is capable of phase transition according to environmental changes, such as pH, light and temperature, to develop different water solubility, and to an imaging method comprising the use of said contrast media.

BACKGROUND ART

The progress in clinical image diagnosis in recent years is remarkable, and various image diagnoses, such as X ray CT (computed tomography), ultrasonic image diagnosis, MRI (magnetic resonance imaging) diagnosis, scintigraphy and the like, have been used to make a diagnosis of almost every part of the body. Along therewith, various contrast media suitable for such image diagnoses have been developed and found to be useful.

In particular, MRI diagnosis is a new diagnostic method which has been drawing much attention recently from the field of radiation diagnosis as well as entire medical fields. When compared to other contrast media, the contrast media for MRI are superior in concentration resolution in tissues and safety from the absence of exposure to X rays, so that they are considered to be clinically useful in locating lesions, grasping anatomical and functional images of normal and abnormal parts, and the like.

On the other hand, the detection capability thereof is not entirely satisfactory, because the detection targets are restricted to certain diseases and parts, and leaves room for the development of contrast media having higher functions.

Contrast media have been awaited that (1) permit detection at lower concentrations (small doses) (2) permit detection of specific target cells (e.g., tumor) with high sensitivity (3) cause no toxicity and (4) are quickly cleared from the body. In particular, the development of an MRI contrast medium has been desired, which has superior contrasting capability, which does not form images where imaging is not desired, such as at normal tissues, and which is capable of forming images only of tumor or specific organs.

It is therefore an object of the present invention to provide an MRI contrast medium having reinforced imaging capability and high function, which is specifically a highly functional MRI contrast medium, which does not form images where imaging is not desired, such as at normal cells, and which expresses imaging capability only at the target cells (e.g., tumor), thereby, in consequence, strikingly improving the detection sensitivity at tumor and the like. The present invention also aims at providing a highly functional MRI contrast medium for angiography, which shows high image forming capability only in blood to increase detection sensitivity.

DISCLOSURE OF THE INVENTION

The present inventors have conducted intensive studies in an attempt to achieve the above-mentioned objects and found that bonding of a polymer responsive to microenvironmental changes to a gadolinium (Gd) type MRI contrast agent successfully results in an MRI contrast medium capable of exhibiting its imaging capability, in other words, capable of on-off switching of imaging capability, only at the target parts. In addition, they have succeeded in achieving even more superior imaging capability by polymerization of said Gd type MRI contrast agent, which resulted in the completion of the invention.

Thus, the present invention provides the following.

(1) A contrast medium comprising a complex of a gadolinium (Gd) type contrast agent and a polymer, said polymer being capable of phase transition in response to environmental changes to develop different water solubility.

(2) The contrast medium of (1) above, wherein the Gd type contrast agent is a polymerized contrast agent.

(3) The contrast medium of (2) above, wherein the polymerized contrast agent has a liner alternating copolymer structure, and which is particularly a complex polymer of the Gd and poly(diethylenetriaminepentaacetic acid (DTPA)- 1,3-propanediamine (PDA)).

(4) The contrast medium of (1) or (2) above, wherein the environmental changes are changes in pH.

(5) The contrast medium of (4) above, wherein the polymer is a member selected from the group consisting of a polydiethylaminoethylmethacrylate (PDEAMA), a poly L-hystidine (PLH), a poly L-lysine (PLL), a poly(1-vinylimidazole) (PVI) and derivatives thereof.

(6) The contrast medium of (1) or (2) above, wherein the environmental changes are changes in light.

(7) The contrast medium of (6) above, wherein the polymer is poly[bis(4-dimethylamino)phenyl](4-vinylphenyl)-methyl-leukohydroxide or a derivative thereof.

(8) The contrast medium of (1) or (2) above, wherein the environmental changes are changes in temperature.

(9) The contrast medium of (8) above, wherein the polymer is poly(N-isopropylacrylamide) or a derivative thereof.

(10) The contrast medium of (1) or (2) above, wherein the environmental changes are changes in expression or distribution of enzyme in a living body.

(11) The contrast medium of (1) above, wherein the Gd type contrast agent is a polymer of a Gd complex and a polymer capable of phase transition in response to environmental changes to develop different water solubility, and the polymer is capable of phase transition in response to the same environmental changes to develop different water solubility.

(12) The contrast medium of (11) above, wherein the environmental changes are changes in pH.

(13) The contrast medium of (12) above, wherein the polymer to be comprised in the Gd type contrast agent and the polymer to be used to form a complex with said Gd type contrast agent are the same or different and each is a member selected from the group consisting of PDEAMA, PLH, PLL, PVI and derivatives thereof.

(14) The contrast medium of (13) above, which does not show imaging capability for a normal tissue but is capable of imaging a tumor tissue and/or an inflammatory tissue.

(15) The contrast medium of (11) above, wherein the Gd type contrast agent is a polymer comprising poly L-lysine and Gd-DTPA.

(16) The contrast medium of any of (1), (2) and (11) above, wherein the contrast medium has been graft copolymerized by further bonding with a synthetic polymer, particularly, a hydrophilic polymer or a polysaccharide.

(17) The contrast medium of (1) or (11) above, wherein the imaging capability can be reversibly controlled in response to environmental changes.

(18) A method for producing a contrast medium comprising a complex of a Gd type contrast agent and a polymer, said polymer being capable of phase transition in response to environmental changes to develop different water solubility.

(19) The method of (18) above, wherein the Gd type contrast agent is a polymerized contrast agent.

(20) The method of (18) or (19) above, wherein the environmental changes are changes in pH.

(21) The method of (20) above, wherein the polymer is a member selected from the group consisting of PDEAMA, PLH, PLL, PVI and derivatives thereof.

(22) The method of (18) above, wherein the Gd type contrast agent is a polymer of a Gd complex and a polymer capable of phase transition in response to environmental changes to develop different water solubility, and the polymer is capable of phase transition in response to the same environmental changes to develop different water solubility.

(23) The method of (22) above, wherein the environmental changes are changes in pH.

(24) The method of (23) above, wherein the polymer to be comprised in the Gd type contrast agent and the polymer to be used to form a complex with said Gd type contrast agent are the same or different and each is a member selected from the group consisting of PDEAMA, PLH, PLL, PVI and derivatives thereof.

(25) An imaging method comprising the use of a contrast medium comprising a complex of a Gd type contrast agent and a polymer, said polymer being capable of phase transition in response to environmental changes to develop different water solubility.

(26) The method of (25) above, wherein the Gd type contrast agent is a polymerized contrast agent.

(27) The method of (25) or (26) above, wherein the environmental changes are changes in pH.

(28) The method of (27) above, wherein the polymer is a member selected from the group consisting of PDEAMA, PLH, PLL, PVI and derivatives thereof.

(29) The method of (25) above, wherein the Gd type contrast agent is a polymer of a Gd complex and a polymer capable of phase transition in response to environmental changes to develop different water solubility, and the polymer is capable of phase transition in response to the same environmental changes to develop different water solubility.

(30) The method of (29) above, wherein the environmental changes are changes in pH.

(31) The method of (30) above, wherein the polymer to be comprised in the Gd type contrast agent and the polymer to be used to form a complex with said Gd type contrast agent are the same or different and each is a member selected from the group consisting of PDEAMA, PLH, PLL, PVI and derivatives thereof.

(32) The method of (31) above, which does not show imaging capability for a normal tissue but is capable of imaging a tumor tissue and/or an inflammatory tissue.

(33) The method of (25) or (29) above, wherein the imaging capability can be reversibly controlled in response to environmental changes.

(34) A commercial package comprising a contrast medium comprising a complex of a Gd type contrast agent and a polymer, said polymer being capable of phase transition in response to environmental changes to develop different water solubility, and a written matter associated therewith, the written matter stating that the contrast medium can or should be used for MRI.

(35) The commercial package of (34) above, wherein the Gd type contrast agent comprises a polymer of a Gd complex and a polymer capable of phase transition in response to environmental changes to develop different water solubility, and the polymer forming the complex with the Gd type contrast agent is capable of phase transition in response to the same environmental changes to develop different water solubility.

DETAILED DESCRIPTION OF THE INVENTION

The imaging mechanism of MRI contrast media differs significantly from that of other contrast media. In X ray contrast media, for example, high degrees of X ray absorption by the contrast media themselves directly affect the brightness of images, whereas in MRI contrast media, the contrast is indirectly made by increasing or decreasing the brightness of images by activating the relaxation of surrounding protons by the contrast media, without direct description of the contrast media themselves. The MRI contrast media are known to include T1 weighted type contrast media and T2 weighted type contrast media Examples of the T1 weighted type contrast media include an ionic complex of a chelating agent and gadolinium (Gd), which is a lanthanide metal highly capable of shortening the proton longitudinal relaxing time (T1). The T1 weighted type contrast media are positive ones which increase brightness of the part where the contrast media are present to make the part shine white in an image. The T2 weighted type contrast media shortens the transverse proton relaxation time (T2) and comprises superparamagnetic iron oxide fine particles (magnetite) prepared into a colloid with a dextran derivative. The T2 weighted type contrast media are negative ones that reduce brightness of the part where the contrast media are present and make the part look dark in an image.

Figure 1:
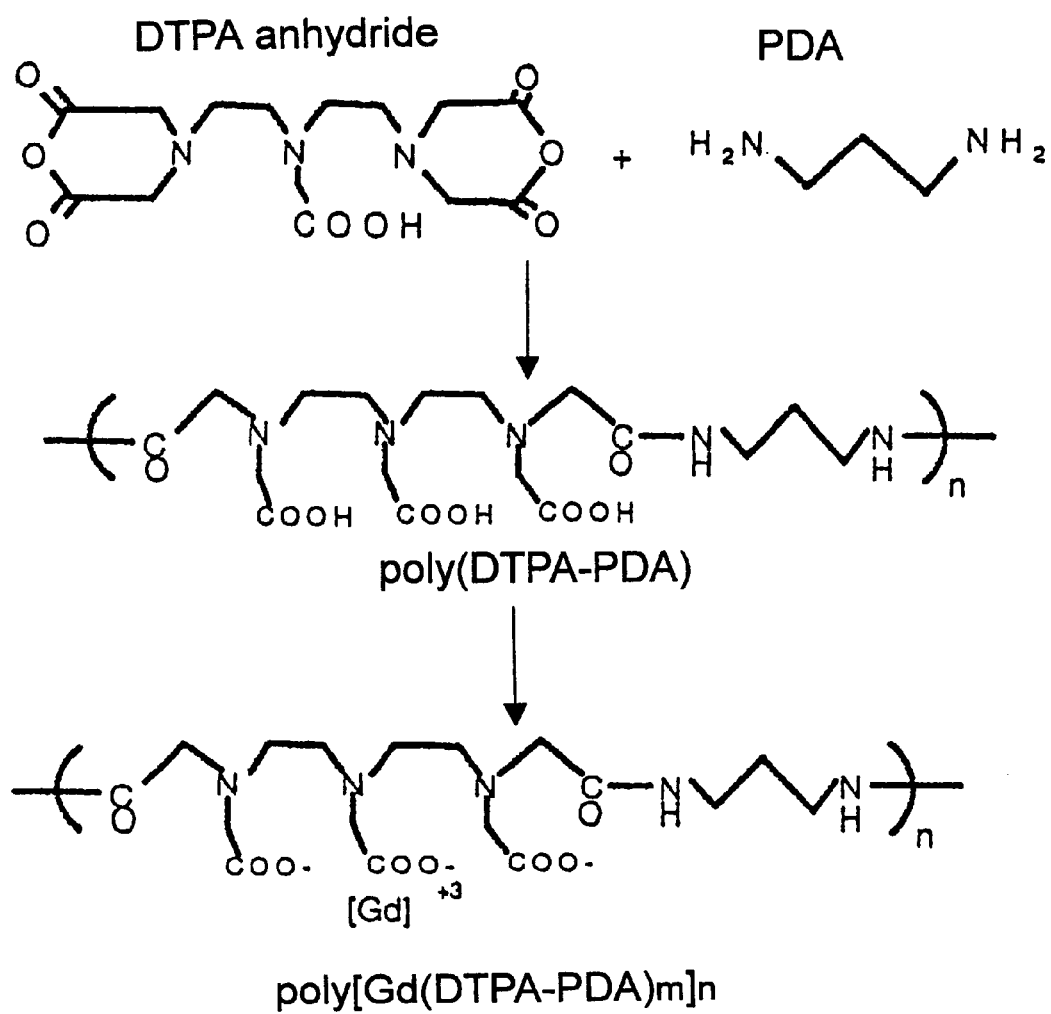
FIG. 1 is a chart showing the synthetic process of poly[Gd(DTPA-PDA)m]n.

The Gd type contrast agent to be used in the present invention is not particularly limited as long as it can be used as a T1 weighted type contrast medium. For superior imaging capability, however, it is preferably polymerized. By the polymerization of the contrast medium, molecular rotation rate can be suppressed and the energy of the MRI contrast medium excited by the magnetic field can be easily transferred on to the surrounding protons, which in turn shortens the proton relaxing time to increase contrasting capability. Preferably, it has a linear structure being expected to show greater suppressive effect on molecular kinetics. When a complex is formed with 1,3-propanediamine (PDA) and then is polymerized, it forms a linear alternating copolymer structure that can be expected to stabilize chelate to a higher degree. Polymerization of the Gd type contrast agent is achieved by the following method which is also shown in FIG. 1.

Diethylenetriaminepentaacetic (DTPA) anhydride, which is a metal chelating agent, and PDA are polymerized by stirring with heating in DMF (N,N-dimethylformamide) to synthesize poly-DTPA-PDA having a molecular weight of 5,000–30,000, preferably 20,000–30,000, wherein DTPA polymerized linearly via PDA. This synthesized product and Gd are mixed in a buffer to introduce Gd into the DTPA moiety to give a Gd complex polymer-comprising MRI contrast medium, i.e., poly[Gd(DTPA-PDA)m]n, wherein m stands for the number of molecules of DTPA-PDA polymer per molecule of Gd and n stands for the number of molecules of Gd(LDTPA-PDA)m polymer per the Gd complex polymer. While the molar ratio of Gd and DTPA is appropriately determined by factors such as retention of high relaxivity, retention of water solubility, charging condition and the like, DTPA is 1 to 60 moles, preferably 2 to 10 moles, more preferably 5 moles, per mole of Gd.

The functional polymer to be used for forming a complex with a Gd type contrast agent in the present invention is not particularly limited as long as it changes phases in response to environmental changes and have different water solubility. However, the polymer is suitably determined according to the changes in the environment to which the polymer responds, diagnostic target part and the like.

The changes in environment to which the polymer responds are exemplified by biological microenvironmental changes, environmental changes induced by physical stimulation from the outside and the like.

The microenvironmental changes in the body may be, for example, changes in pH, changes in expression of enzymes, changes in glucose concentration and the like, and the environmental changes are induced by physical stimulation from the outside such as temperature, light, ultrasonic sound, magnetic field and the like. When the light is used to cause environmental changes as a result of physical stimulation from the outside, the polymer to be bonded may be poly[bis(4dimethylamino)phenyl](4-vinylphenyl)methylleukohydroxide or a derivative thereof, and when the temperature is used to cause such changes, poly(N-isopropylacrylamide) or a derivative thereof may be used.

When changes in pH are used, specifically for example, when pH changes in tissues (e.g., tumor tissue) having a weak acidic pH unlike normal tissues are used, polydiethylaminoethylmethacrylate (PDEAMA), poly 1-hystidine (PLH), poly(1-vinylimidazole) (PVI) and derivatives thereof, which undergo phase transit in weak acidic environment, are preferably used. When pH changes to the alkaline range are used, poly L-lysine (PLL) and derivatives thereof, which undergo phase transit in alkaline environment, are preferably used.

The phase transit generally means a phenomenon in which a substance changes from one phase to another according to the changes of certain conditions. In the present invention, the term means transit from a dissolution state to a deposition state and vice versa. More specifically, it means transfer between dissolution state and coacervate state, which occurs reversibly in the present invention in response to environmental changes. Note that a phenomenon of phase separation between a high concentration phase and a low concentration phase of a solution of a polymer mixture is called coacervation, wherein the high concentration polymer liquid phase is called a coacervate after the shape of its miniscule drop.

For example, PDEAMA, which is a pH responsive polymer, changes phases at around pH 7.5, PLH and PVI changes phases at around pH 6.5, and PLL changes phases at around pH 10.

The complex of a polymer responsive to environmental changes and the Gd type MRI contrast agent can be generally prepared by mixing-stirring them in an aqueous solution having a pH of not more than the phase transition point at room temperature, though subject to variation depending on the polymer to be used. For example, for the synthesis of a complex of a pH responsive polymer, said pH responsive polymer and a Gd type MRI contrast agent are mixed at a pH not greater than the phase transit pH. When PDEAMA is used, for example, the ingredients are mixed in an aqueous solution at a pH of around 5–7, preferably around 6.5, at room temperature to obtain a complex. When PLH or PVI are used, the ingredients are mixed in an aqueous solution at a pH of around 4–6, preferably around 6, at room temperature to obtain a complex. When PLL is used, the ingredients are mixed in an aqueous solution at a pH of around 7–9, preferably around 8.5, at room temperature to obtain a complex.

In another embodiment of the present invention, a polymer of a Gd complex and a polymer capable of phase transition in response to environmental changes to develop different water solubility is preferably used as a Gd contrast agent, particularly as a polymerized Gd contrast agent. The contrast medium of the present invention can be prepared by forming a complex of said polymer and the above-mentioned polymer capable of phase transition in response to environmental changes to develop different water solubility. The environmental changes to respond to are exemplified by those mentioned above, which are specifically small environmental changes seen in the living body, such as changes in pH, changes in the expression of enzyme, changes in glucose concentration and the like, and environmental changes caused by external physical stimulation such as temperature, light, ultrasound and magnetic field. Preferred are changes in pH. The polymer that is capable of phase transition in response to environmental changes applied to form a polymer with a Gd complex and that develops different water solubility is exemplified by those mentioned above. For example, PLL, PDEAMA, PLH and PVI are used for changes in pH, with more preference given to PLL. The chelating agent to be used for preparing the Gd complex is free of any limitation as long as it can make a complex with Gd. Preferred is DTPA mentioned above, which is used in a broad range of applications in this field. A bonding of a Gd complex and a polymer as exemplified above can be conducted according to a method known in this field, though subject to variation depending on the polymer to be used. When Gd-DTPA is used as the Gd complex and PLL is used as the polymer, the bonding can be conducted according to a method disclosed in EP-B-0331616 (Example 37). The amino group of PLL and one of the five carboxyl groups of DTPA are covalently bonded to synthesize PLL-DTPA and Gd ions are added to give PLL(Gd-DTPA). The polymer capable of phase transition in response to environmental changes to develop different water solubility, which is used to form a complex with the obtained Gd type contrast agent, vanes depending on the environment to respond to and is exemplified by those mentioned above. In case of changes in pH, for example, PLL, PDEAMA, PLH and PVI are used.

The proportion of the polymer to the Gd contrast agent may vary according to the kind of Gd contrast agent and polymer to be used, as well as the conditions under which the complex is formed. The charging ratio is generally Gd contrast agent:polymer=1:0.2–10, preferably 1:0.5–10, and more preferably 1:1–3. Particularly when a polymer of a Gd complex and a polymer capable of phase transition in response to environmental changes to develop different water solubility is used as the Gd type contrast agent, said contrast agent preferably has a contrast agent: polymer ratio of 1:0.2–5, more preferably 1:0.8–1.2. The DTPA has many carboxyl groups, and the Gd type contrast agent comprising the Gd complex obtained by the use of said DTPA is an anionic polymer as a whole. On the other hand, pH responsive polymers such as PDEAMA, PLL and PLH are cationic polymers having amino group. The both are complexed by ionic interaction to give a polyionic complex The inventive contrast medium comprising said polyionic complex can show less imaging capability in the pH range of from about 4 to about 9, preferably from about 6 to about 8. When the pH deviates from said range, the imaging capability can be increased. Such variation in imaging capabilities is achieved in a reversible manner in response to pH.

In the present invention, the above-mentioned contrast medium is preferably bonded with a hydrophilic synthetic polymer, polysaccharides and the like. Said synthetic polymer and polysaccharides can be bonded by graft copolymerization with the polymer (main chain polymer) responsive to the environment, that is used to form a complex with a Gd type contrast agent. For a bonding of the main chain polymer, which is a polymer responsive to the environmental changes, and the above-mentioned synthetic polymer or polysaccharides, a conventional method generally used to synthesize graft copolymers can be utilized, though the method varies depending on the main chain polymer, synthetic polymer and polysaccharides to be used.

Examples of the synthetic polymer suitably used in the present invention include polyethylene, polyethylene glycol, polyoxyethylene glycol, polyethylene terephthalate, polypropylene, polypropylene glycol, polyurethane, polyurethaneurea, pullulonic acid, pullulonic alcohol, polyvinyl polymer, polyvinyl alcohol, polyvinyl chloride, polyvinylpyrrolidone, nylon, polystyrene, polylactate, hydrocarbon fluoride, carbon fluoride, polytetruoroethylene, polyacrylate, polyacrylic acid, polymethacrylic acid, polyacrylamide and the like, and their derivatives. In the present invention, those having a molecular weight of about 1,000–100,000, preferably about 5,000–50,000, are used.

Examples of the polysaccharides suitably used in the present invention include arabinan, fluctane, fucan, arabinogalactane, galactane, galacturonan, glucan, mannan, xylane, levan, fucoidan, carrageenan, galactocallolose, pectin, pectinic acid, amylose, pullulan, glycogen, amylopectin, cellulose, dextran, pustulan, chitin, agalose, keratin, chondroitin, dermatan, hyaluronic acid, arginic acid, xanthan gum, starch, carbonymethylcellulose, hydroxymethylcellulose, hydroxypropylmethylcellulose, methylcellulose, methoxylcellulose, ethrose, threose, ribose, arabinose, xylose, lyxose, allose, altrose, glucose, mannose, gulose, idose, galactose, talose, erythrulose, ribulose, xylulose, psicose, fluctose, sorbose, tagatose, glucuronic acid, gluconic acid, glucaric acid, galacturonic acid, mannuronic acid, glucosamine, galactosamine, neuraminic acid and the like. Those having a molecular weight of about 300–10,000, preferably about 1,000–5,000, are used, without particular limitation on the origin thereof.

The above-mentioned graft copolymer has a core-shell structure. This structure conceals the polymerized Gd contrast agent in the highly hydrophobic core part, and does not allow Gd to be in contact with the protons of the surrounding water, thereby inhibiting image forming. In addition, since the shell part contains a hydrophilic polymer, it retains water solubility as a whole. The hydrophilicity suppresses interaction in the living body, such as adsorption of biological components (e.g., protein), avoiding intake thereof into reticuloendothelial system, which in turn may prolong residence in blood. Moreover, the specific targeting, namely, targeting particular organs and cells by utilizing specific sugar chain recognizing function, may be achieved.

After delivery to the target part, the main chain polymer responds to the pH of the tissue and changes phases. As a result, imbalance of charge occurs, resulting in failure to maintain the core-shell structure. Then, Gd contacts the protons of the surrounding water and expresses its image forming capability.

When imaging a tumor and the like, for example, since the pH of blood and normal tissues is from neutral to weak alkaline, imaging cannot be performed as long as the core-shell structure is maintained in said pH range. The imaging occurs only when the structure is placed in a weak acidic tumor. In angiography, it is designed that imaging occurs in blood having a pH of from neutral to weak alkaline by not maintaining the core-shell structure, and the core-shell structure is reconstructed upon migration into weak acidic lysosome and the like to turn off the imaging capability. Accordingly, images are formed only at the target parts and contrariwise at other parts, whereby a relatively high detection sensitivity can be achieved. In particular, when a polymer of a Gd complex and a polymer, such as PLL and PDEAMA, is used as the Gd type contrast agent to prepare a complex with a pH responsive polymer such as PLL and PDEAMA, a tumor tissue and a lesion suffering from inflammation can be effectively imaged.

Figure 2:
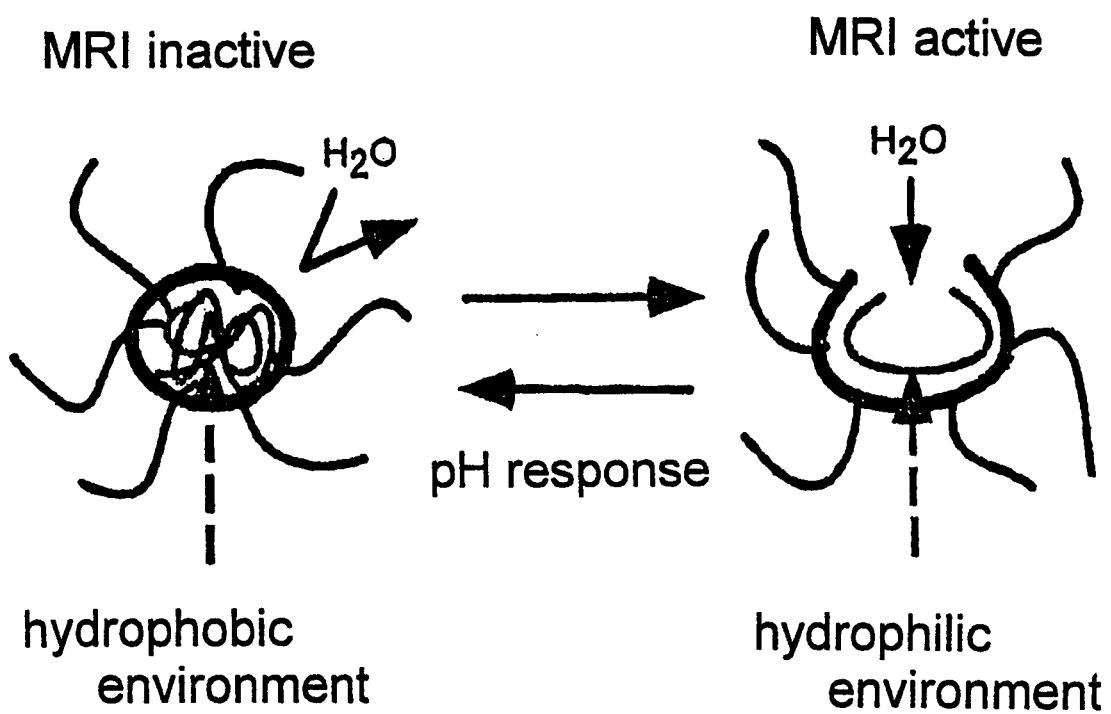
FIG. 2 is a schematic showing of the on-off switching function in response to variations in pH of the inventive MRI contrast medium.

The structural changes of said complex according to pH changes are mathematically shown in FIG. 2.

The reversible switching of the imaging capability of the inventive contrast medium is considered to be attributable to reversible control of the phase transit, thereby inducing interaction between Gd molecules and water molecules in the vicinity thereof; namely, control of transmission of Gd energy excited by electromagnetic wave to the water molecule around the Gd molecules.

The contrast medium of the present invention can be used normally in the form of a suspension or solution in a solvent such as distilled water for injection, physiological saline and Ringer solution. Where necessary, a pharmacologically acceptable additives such as carrier, excipient and the like can be added. This contrast medium can be applied to cells and the like, and also can be administered to a living body by way of intravascular (vein, artery) administration, oral administration, rectal administration, vaginal administration, lymph duct administration, intraarticular administration and the lie. Preferably, it is administered in the form of an aqueous agent, emulsion or suspension. The additives to be used for the contrast medium of the present invention vary depending on the mode of administration, administration route and the like. Specific examples in the case of injection include buffers, antibacterial agents, stabilizers, solubilizers and excipients which are used alone or in combination. In the case of an agent for oral administration, such as aqueous agent, syrup, emulsion and suspension, coloring agents, preservatives, stabilizers, suspending agents, emulsifying agents, thickeners, sweeteners, aromatics and the like are used alone or in combination. Various additives generally used in the pertinent field are used for this end.

The inventive contrast medium for MRI can be administered to form images according to the method used for conventional MRI contrast medium. Specifically, intravenous administration and oral administration can be employed. While the specific dose varies according to the age of administration subjects, the size of body, the parts to be imaged and the like, it is generally 5–100 $\mu$mol/kg, preferably 10–50 $\mu$mol/kg, in the amount of the Gd type contrast agent contained therein, namely, in the amount of Gd.

The contrast medium of the present invention can be suitably used as a contrast medium for various animals besides human, and the mode of administration, administration route and dose are appropriately determined according to the body weight and conditions of the target animal.

EXAMPLES

The present invention is described in more detail by illustrative Examples and Experimental Examples, to which the present invention is not limited.

Example 1

Synthesis of poly[Gd(DTPA-PDA)m]n (1) Synthesis of poly(DTPA-PDA)

DTPAA (diethylenetriaminepentaacetic anhydride, 12 mM, manufactured by Dojindo) was dissolved in 20 ml of DMF (N,N-dimethylformamide) by heating at 60° C. Separately, a solution of PDA (1,3-propanediamine, 12 mM, manufactured by Wako) and TEA (triethylamine, 50 mM, manufactured by Wako) respectively dissolved in 20 ml of DMF was prepared. Then both solutions were mixed by stirring at 60° C. for 24 hours. The resulting mixture was evaporated at 80° C. to solidness and dissolved in about 30 ml of water. This aqueous solution was precipitated with 100% ethanol. The precipitation was collected by filtration and dried to give 5.7 g of crude poly-DTPA-PDA. For further purification, the obtained crude poly-DTPA-PDA was re-dissolved in 30 ml of water and ultrafiltrated (fraction molecular weight: 5000d) to give 0.8 g of purified poly-DTPA-PDA.

An aqueous solution (1 ml) of 0.1 M gadolinium (Gd) and poly-DTPA-PDA (86.2 mg) obtained in above (1) were mixed in a 0.1 M phosphate buffer (pH 7.2) at room temperature (Gd:DTPA molar ratio=1:2) to introduce Gd into the DTPA moiety, thereby producing poly[Gd(DTPA-PDA)2]35. In the same manner, Gd and DTPA were mixed at a molar ratio of Gd:DTPA=1:5 to give poly[Gd(DTPA-PDA)5]14.

Example 2

Evaluation of poly[Gd(DTPA-PDA)m]n

The proton relativity of poly[Gd(DTPA-PDA)2]35 and poly[Gd(DTPA-PDA)5]14 obtained in Example 1 was compared with that of conventional MRI contrast medium. As the conventional MRI contrast medium, used was Gd-DTPA (Magnevist). The proton relaxivity was determined by using Minispec (NMS 120/125/10VTS, manufactured by Japan Bruker) at frequency at 20 MHz and temperature at 40° C. T1 was determined using an IR (inversion recovery) method under the conditions of initial $\tau$ of 2 ms, $\tau$ magnification of 1.7 and determination points of 20. T2 was determined using a CPMG (Carr-Purcell-Meiboon-Gill) method under the conditions of $\tau$ of 1 ms and determination points of 50.

Respective proton relaxing times (T1 and T2) are shown in Table 1, and the proton relaxivity (R1 and R2) calculated from said proton relaxing time are shown in Table 2.

TABLE 1

Effects of polymerization of MRI contrast medium on T1 and T2 relaxing time

| Gd concentration (mM) | Gd-DTPA | poly[Gd(DTPA-PDA)2]35 | poly[Gd(DTPA-PDA)5]14 |
|---|---|---|---|
| T1 relaxing time (msec.) | | | |
| 0.1 | 1503 | 927 | 1035 |
| 1 | 247 | 120 | 130 |
| 5 | 53 | 25 | 27 |
| 10 | 26 | 13 | 14 |
| T2 relaxing time (msec.) | | | |
| 0.1 | 1339 | 843 | 927 |
| 1 | 220 | 106 | 114 |
| 5 | 47 | 22 | 24 |
| 10 | 24 | 11 | 12 |

TABLE 2

Effects of polymerization of MRI contrast medium on proton relaxivity

| Sample | relaxivity (1 mmol$^{-1}$ sec$^{-1}$) | |
|---|---|---|
| | R1 | R2 |
| Gd-DTPA | 3.81 | 4.20 |
| poly[Gd(DTPA-PDA)2]35 | 7.96 | 9.10 |
| poly[Gd(DTPA-PDA)5]14 | 7.29 | 8.57 |

Polymerization of the Gd type MRI contrast medium via PDA resulted in two times or more higher values of proton relaxivity per unit Gd than Gd-DTPA.

Example 3

Preparation of Graft Copolymer of PLL and Dextran 100 mg of PLL·HCl salt (manufactured by Peptide Institute Inc.) and 100 mg of dextan (Mw=2,600, manufactured by Funakoshi) were placed in 15 ml of 0.1 M borate buffer (pH 8.5), and 0.3 M sodium cyanoborohydride was added. The mixture was reacted at 45° C. for 2 days to give PLL-g-dextran (graft rate of dextran is 6%).

Example 4

Preparation of Graft Copolymer of PLL and Hyaluronic Acid 100 mg of PLL HCl salt (manufactured by Peptide Institute Inc.) and 100 mg of hyaluronic acid (Mw=8,000, manufactured by DENKI KAGAKU KOGYO KABUSHIKI KAISHA) were placed in 15 ml of 0.1 M borate buffer (pH 8.5) and 0.3 M sodium cyanoborohydride and 0.4 M NaCl were added. The mixture was reacted at 37° C. for 2 days to give PLL-g-hyaluronic acid (graft rate of hyaluronic acid is 2%).

Example 5

Preparation of Mixed Solution of PDEAMA and poly[Gd(DTPA-PDA)m]n 4.6 mg of PDEAMA (polydiethylaminoethylmethacrylate) was added to 100 μl of the aqueous solution of poly[Gd(DTPA-PDA)5]14 (20 mM Gd/L, 46.24 mg polymer/ml) obtained in Example 1 and mixed (each ingredient has equal charge at this volume proportion). Water was added to make the total amount 1 ml.

Example 6

Preparation of Mixed Solution of PLH and poly[Gd(DTPA-PDA)m]n 4 mg of PLH (poly-L-hystidine, manufactured by Sigma) was added to 100 μl of the aqueous solution of poly[Gd (DTPA-PDA)5]14 (20 mM Gd/L, 46.24 mg polymer/ml) obtained in Example 1 and mixed (each ingredient has equal charge at this volume proportion). Water was added to make the total amount 1 ml.

Example 7

Preparation of Mixed Solution of PLL-g-dextran and poly[Gd(DTPA-PDA)m]n 7.25 mg of PLL-g-dextran (Mw of dextran is 2,600 and graft rate of dextran is 6%) obtained in Example 3 was added to 100 μl of the aqueous solution of poly[Gd(DTPA-PDA) 5]14 (20 mM Gd/L, 46.24 mg polymer/ml) obtained in Example 1 and mixed (each ingredient has equal charge at this volume proportion). Water was added to make the total amount 1 ml.

Example 8

Acid-base Titration of Mixed Solution of poly[Gd(DTPA-PDA)5]14 and PDEAMA or PLH 50 μl of 1N HCl was added to the mixed solution of poly[Gd(DTPA-PDA)5]14 and PDEAMA or PLH obtained in Examples 5 and 6, and pH thereof was adjusted to an acidic one. Then, 2 μl of 1N NaOH was dropwise added and pH was respectively determined. Simultaneously, the state of the mixed solutions was observed. The results are summarized in the following Table 3.

TABLE 3

Phase transit behavior and pH of mixed polymer solution

| | pH of phase transit | | |
|---|---|---|---|
| mixed solution | dissociation of complex | formation of complex | dissociation of complex |
| PDEAMA + poly[Gd(DTPA-PDA)5]14 | 3.8 or below | 3.8–7.8 | 7.8 or above |
| PLH + poly[Gd(DTPA-PDA)5]14 | 3.7 or below | 3.7–5.6 | 5.6 or above |

When poly[Gd(DTPA-PDA)5]14 and PDEAMA or PLH were mixed, all of which having the same charge, the both mixed solutions did not form a complex but were in a solution state at a pH of not more than 3.8. The complex-forming pH range was from 3.8 to 7.8 for PDEAMA, and from 3.7 to 5.6 for PLH. At a pH range above this range, PDEAMA and PLH were completely de-protonated and precipitated, showing release of poly[Gd(DTPA-PDA)5]14.

Example 9

Preparation of Complex of poly[Gd(DTPA-PDA)5] 14 and PDEAMA in a Solution Having Various pHs (5–9)

The poly[Gd(DTPA-PDA)5]14 prepared in Example 1 was added to a solution (1 ml, at pH 5) so that the Gd concentration was 2 mM. To this solution was added 4.6 mg of PDEAMA and pH was adjusted to a predetermined value (5–9) with a suitable amount of 1N NaOH. Mixing of the same for one hour at room temperature (each ingredient had equal charge at this volume proportion) gave a complex.

Example 10

Preparation of Complex of poly[Gd(DTPA-PDA)5] 14 and PLH in a Solution Having Various pHs (5–9)

The poly[Gd(DTPA-PDA)5]14 prepared in Example 1 was added to a solution (1 ml, at pH 5) so that the Gd concentration was 2 mM. To this solution was added 4.5 mg of PLH and pH was adjusted to a predetermined one (5–9) with a suitable amount of 1N NaOH. Mixing of the same for one hour at room temperature (each ingredient had equal charge at this volume proportion) gave a complex.

Example 11

Determination of T1, T2 Relaxing Times of Complexes of poly[Gd(DTPA-PDA)5]14, and PDEAMA or PLH, at Various pHs.

Figure 3:
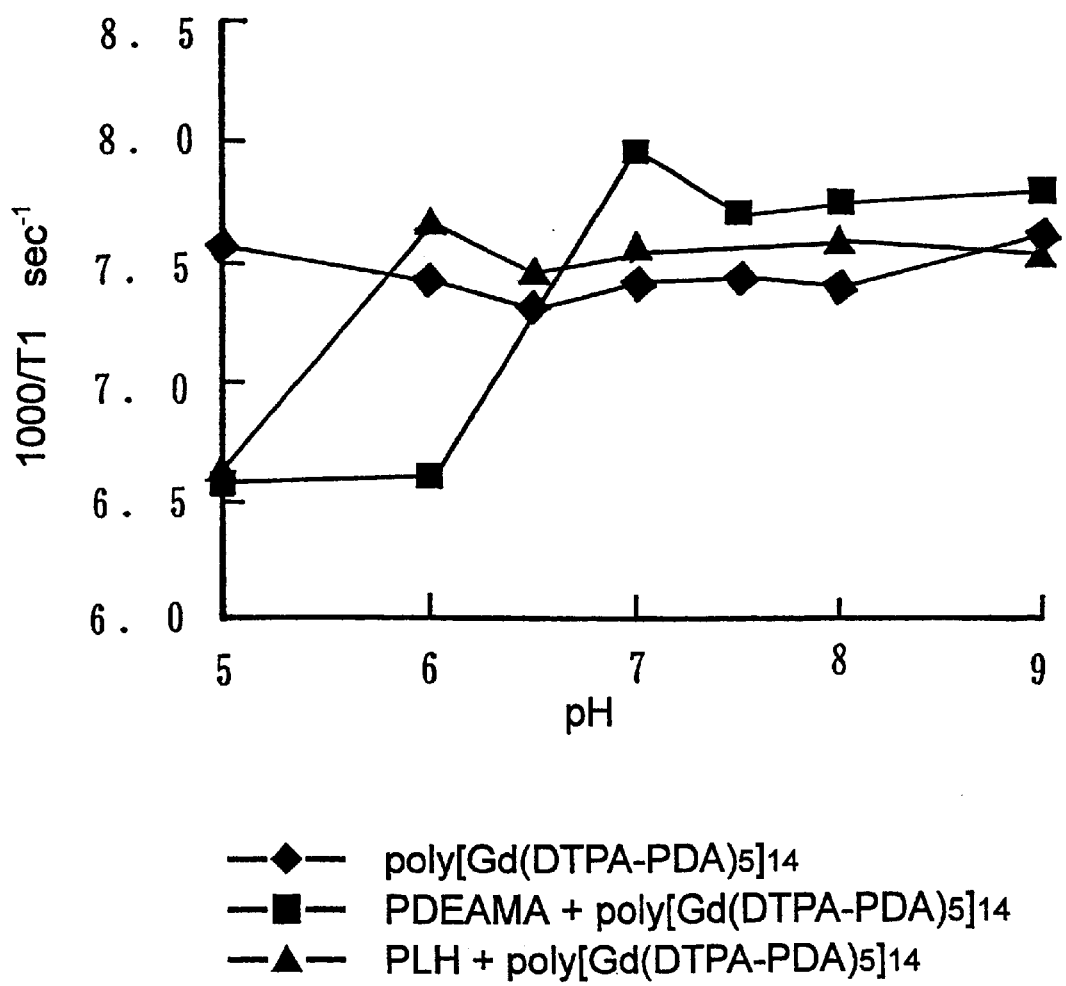
FIG. 3 shows the relationship between pH and the reciprocal of T1 relaxing time with respect to the complex of poly[Gd(DTPA-PDA)5]14, and PDEAMA or PLH, wherein -♦- shows poly[Gd(DTPA-PDA)5]14 alone, -■- shows a complex of poly[Gd(DTPA-PDA)5]14 and PDEAMA, and -▲- shows a complex of poly[Gd(DTPA-PDA)5]14 and PLH.
Figure 4:
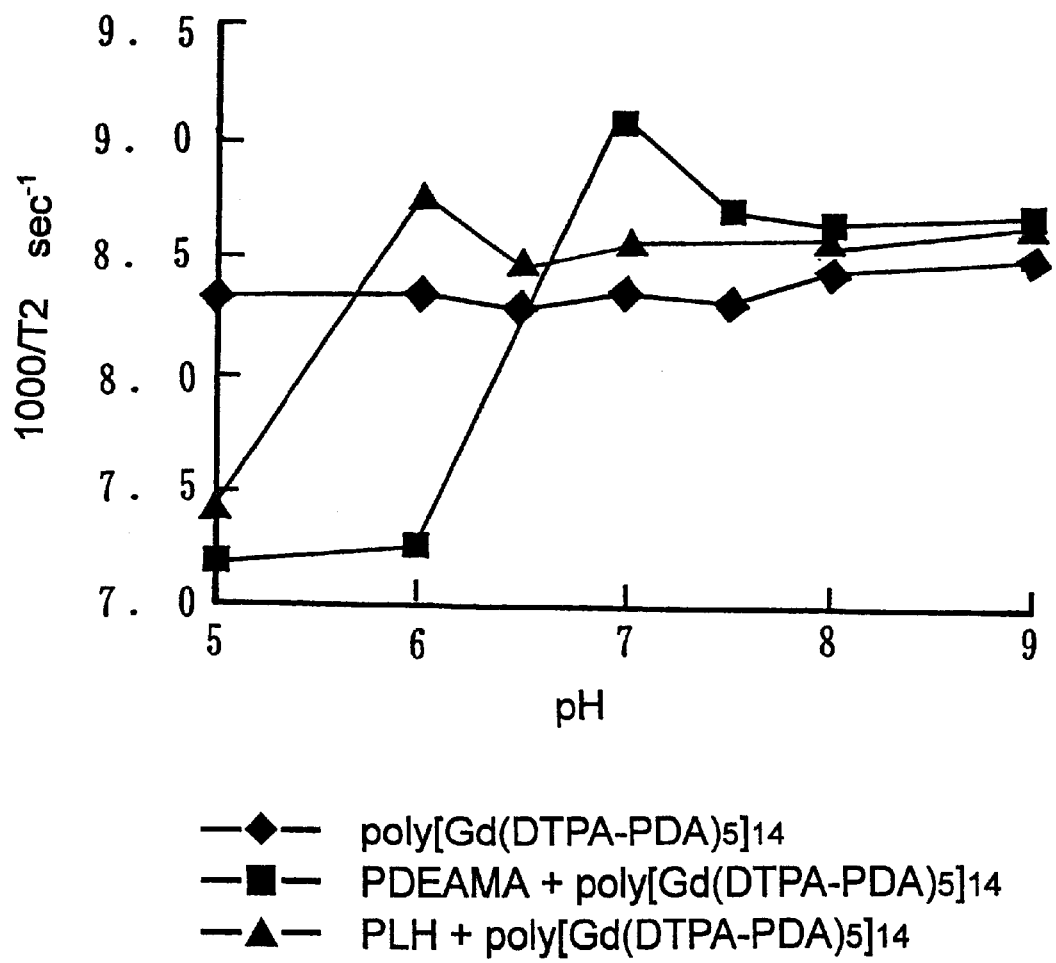
FIG. 4 shows the relationship between pH and the reciprocal of T2 relaxing time with respect to the complex of poly[Gd(DTPA-PDA)5]14, and PDEAMA or PLH, wherein -♦- shows poly[Gd(DTPA-PDA)5]14 alone, -■- shows a complex of poly[Gd(DTPA-PDA)5]14 and PDEAMA, and -▲- shows a complex of poly[Gd(DTPA-PDA)5]14 and PLH.

The relationship was examined between the reciprocals of T1 and T2 relaxing times and pH of the complexes of poly[Gd(DTPA-PDA)5]14, and PDEAMA or PLH, at each pH, prepared in Examples 9 and 10. The results show that the higher the values of reciprocals of T1 and T2 relaxing time were the higher imaging capabilities were. As a control, poly[Gd(DTPA-PDA)5]14 alone prepared in Example 1 was used. The T1 and T2 relaxing times were measured in the same manner as in Example 2. The relationship between the reciprocal of T1 relaxing time and pH is shown in FIG. 3, and the relationship between the reciprocal of T2 relaxing time and pH is shown in FIG. 4.

The poly[Gd(DTPA-PDA)5]14 did not show variations in imaging capability throughout all pHs. However, the complex thereof with PDEAMA showed drastic changes in the imaging capability at a pH of not less than 7.5, and the complex thereof with PLH showed drastic changes in the imaging capability at a pH of not less than 6.5.

Example 12

Figure 5:
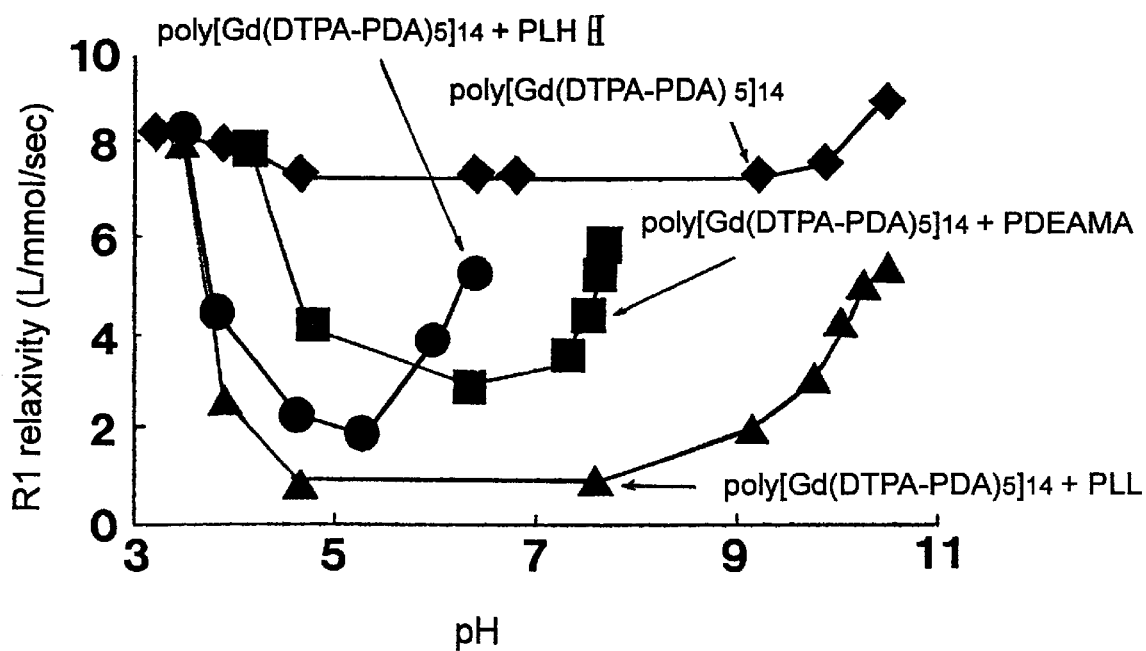
FIG. 5 shows the relationship between pH and the R1 relaxivity (reciprocal of T1 relaxing time) with respect to the complex of poly[Gd(DTPA-PDA)5]14, and PDEAMA or PLH or PLL, wherein -♦- shows poly[Gd(DTPA-PDA)5]14 alone, -■- shows a complex of poly[Gd(DTPA-PDA)5]14 and PDEAMA, -▲- shows a complex of poly[Gd(DTPA-PDA)5]14 and PLL, and -●- shows a complex of poly[Gd(DTPA-PDA)5]14 and PLH.

Determination of R1 Relaxivity of Complexes of poly[Gd(DTPA-PDA)5]14, and PDEAMA, PLH or PLL, at Various pHs (a) Preparation of Mother Liquor
(1) Poly[Gd(DTPA-PDA)5]14 mother liquor, prepared according to Example 1, 46.3 mg/ml·0.15 M NaCl
(2) PDEAMA mother liquor, prepare according to following Example 13(b), 44.95 mg/ml·0.15 M NaCl
(3) PLL mother liquor; prepared using PLL·HCl salt (Peptide Institute, Inc.), 39.4 mg/ml·0.15 M NaCl
(4) PLH mother liquor, prepared using PLH·HCl salt (Sigma), 41.3 mg/ml·0.15 M NaCl
(b) Measurement Method To the following samples was added 2 μl of 1N NaOH to cause changes in pH from approximately 3 to 10, and T1 relaxing time was measured in the same manner as in Example 2 using Minispec. The reciprocal thereof, i.e., R1 relaxivty, was calculated. The results are shown in FIG. 5. The measurement was done immediately after preparation of the samples.

<Samples> poly[Gd(DTPA-PDA)5]14 solution alone: 0.15 M NaCl was added to 50 μl of the solution of this Example (a) (1) to make the total amount 1 ml poly[Gd(DTPA-PDA)5]14 +PDEAMA: 0.15 M NaCl was added to 50 μl of the solution of this Example (a) (1) and 50 μl of the solution of this Example (a) (2) to make the total amount 1 ml poly[Gd(DTPA-PDA)5]14 +PLL: 0.15 M NaCl was added to 50 μl of the solution of this Example (a) (1) and 50 μl of the solution of this Example (a) (3) to make the total amount 1 ml poly[Gd(DTPA-PDA)5]14 +PLH: 0.15 M NaCl was added to 50 μl of the solution of this Example (a) (1) and 50 μl of the solution of this Example (a) (4) to make the total amount 1 ml (c) Results When poly[Gd(DTPA-PDA)5]14 was used alone, R1 relaxivity did not show significant changes throughout the entire pH range. When mixed solutions with PDEAMA, PLL or PLH were used, pH-dependent changes of R1 were observed.

The pH values at which decrease, minimum value and recovery of R1 were observed are shown in Table 4.

TABLE 4

| Polymer constituting the complex | pH | | |
| --- | --- | --- | --- |
| | Decrease of R1 | Minimum value of R1 | Recovery of R1 |
| PDEAMA | near 5 | near 6.5 | near 7.5 |
| PLL | near 4 | near 7 | near 9 |
| PLH | near 4 | near 5 | near 6 |

Therefore, when a complex of poly[Gd(DTPA-PDA)5]14 and PDEAMA is used as an MRI contrast medium, for example, it does not show imaging activity in a weak acidic to neutral range, because a complex structure is formed in the state that PDEAMA encloses the poly[Gd(DTPA-PDA) 5]14 contrast medium in the inner hydrophobic part. In a weak alkaline range, however, PDEAMA undergoes phase transit to permit release of the poly[Gd(DTPA-PDA)5]14 contrast medium, which then comes into contact with the surrounding protons and shows an imaging activity.

Example 13

Relationship Between Formation of Complex and pH with Respect to PLL(Gd-DTPA) (16%) Solution, PDEAMA Solution and a Mixture of the both (a) Preparation of PLL(Gd-DTPA) (16%) solution PLL(Gd-DTPA) was obtained from Schering AG (Berlin, Germany). In this example, a PLL(Gd-DTPA) (16%) wherein Gd had been introduced into 16% of the DTPA moiety was prepared and used. PLL(Gd-DTPA) was dialyzed against 0.1 M EDTA solution for 4 days and then against water for one week (MWCO=3,500) to produce a polyanion state wherein Gd ions were dissociated. The resulting solution was lyophilized and stored until use. The PLL(Gd-DTPA) (16%) in this state is shown in the following (hereinafter this substance is referred to by the symbol [I]).

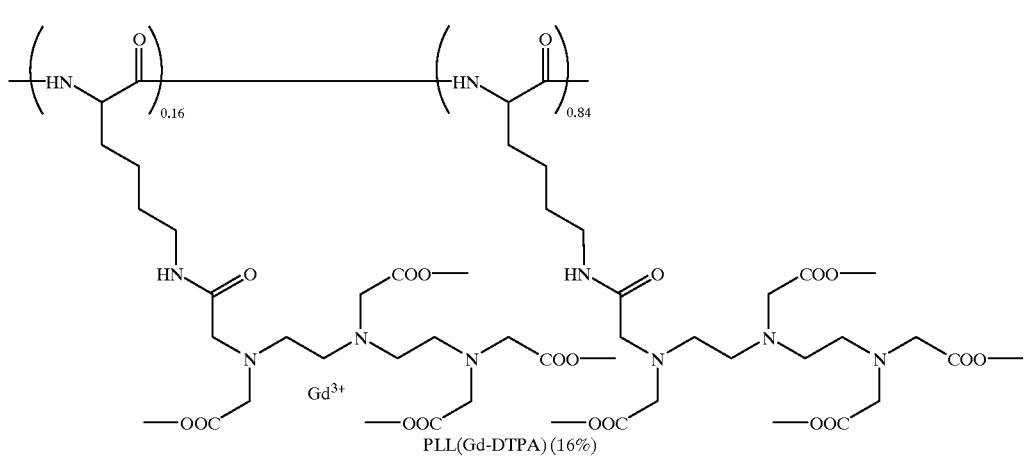

PLL(Gd-DTPA)(16%)

The [Gd]/[DTPA unit] ratio of [I] was confirmed by ICP according to the Experimental Example 2 to be mentioned later and found to be 0.16. Then, the number average molecular weight of [I] was measured by GPC (gel permeation chromatography). The GPC was conducted using JASCO880-PU pump system under the conditions of flow rate 0.8 ml/min (25° C.) and ultrahydrogel 1000 column (Japan Waters Ltd.) As the mobile phase, an aqueous solution containing 0.5 M acetic acid and 0.3 M sodium sulfate was used. The polymer was detected by refractive index detector (830-RI, JASCO) and multiangle light scattering detector (Dawn-DSP, Wyatt Technology). The number average molecular weight of [I] was $5 \times 10^4$.

(b) Preparation of PDEAMA

The poly[2-(dimethylamino)ethylmethacrylate] (hereinafter this compound is referred to by the symbol [II]) of the following formula

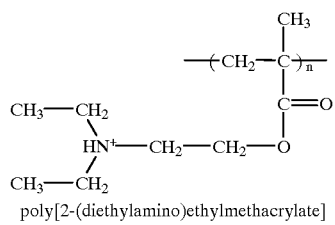

poly[2-(diethylamino)ethylmethacrylate]

was prepared from the corresponding monomer, DEAMA, by radical polymerization in DMF in the presence of 2,2'-azobis(2,4-dimethylvaleronitrile), which is a polymerization initiator, in vacuo at 45° C. for 3 days.

After polymerization, excess acetonitrile was added to this solution with stirring to allow the polymer fill to precipitate. This solution was subjected to ultrafiltration using a cellulose triacetate membrane (MWCO=20,000, Sartorius) to recover polymer [II].

The number average molecular weight of [II] was $8.6 \times 10^4$.

(c) Measurement of turbidity

Formation of a complex of PLL(Gd-DTPA) (16%) and PDEAMA was examined at various pHs by the changes in turbidity associated with the complex formation.

Figure 6:
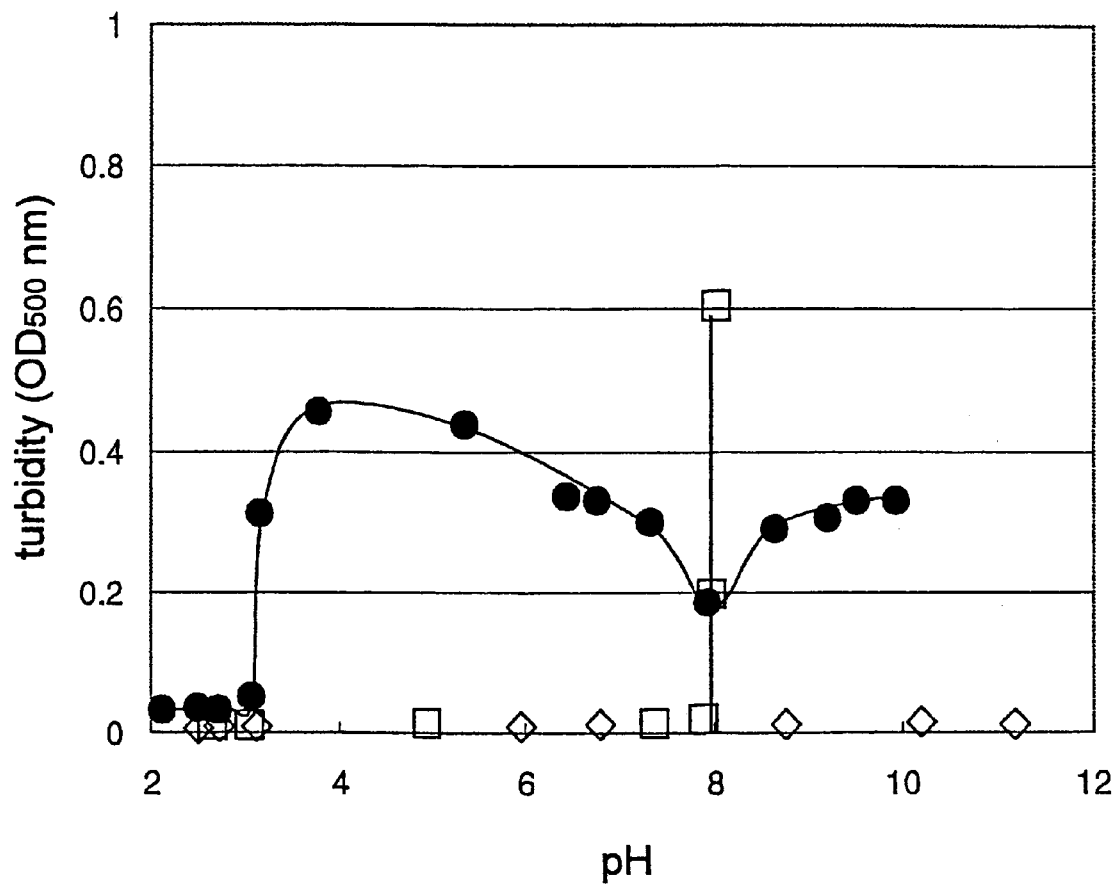
FIG. 6 shows the relationship between turbidity and pH of the solutions of PLL(Gd-DTPA) (16%), PDEAMA and a mixture of the two, wherein -◇-shows PLL(Gd-DTPA) (16%) alone, -□- shows PDEAMA alone, and -●- shows a mixture of PLL(Gd-DTPA) (16%) and PDEAMA.

A 0.15 M NaCl solution (3.4 mg/ml) of [I] prepared in this Example (a), a 0.15 M NaCl solution (3.8 mg/ml) of [II] prepared in this Example (and a mixture of equal amounts of these two solutions were titrated with 0.1 M NaOH solution by changing pH of the solutions. The pH value was measured by TOA HM-20E pH meter. The turbidity of the solution under titration was evaluated by measuring absorbance at 500 nm with Beckman DU-640 spectrophotometer. The results are shown in FIG. 6. The formation of the turbidity was started from around the pH just over 3 and this suggests that the formation of a polyionic complex is started from around this pH value. The turbidity was observed up to pH 8 and suddenly disappeared at pH 8. Subsequently, the second changes in turbidity were observed, which appears to be due to nearly complete deprotonization of [II] at pH 8, resulting in dissociation thereof from the complex.

Example 14

Figure 7:
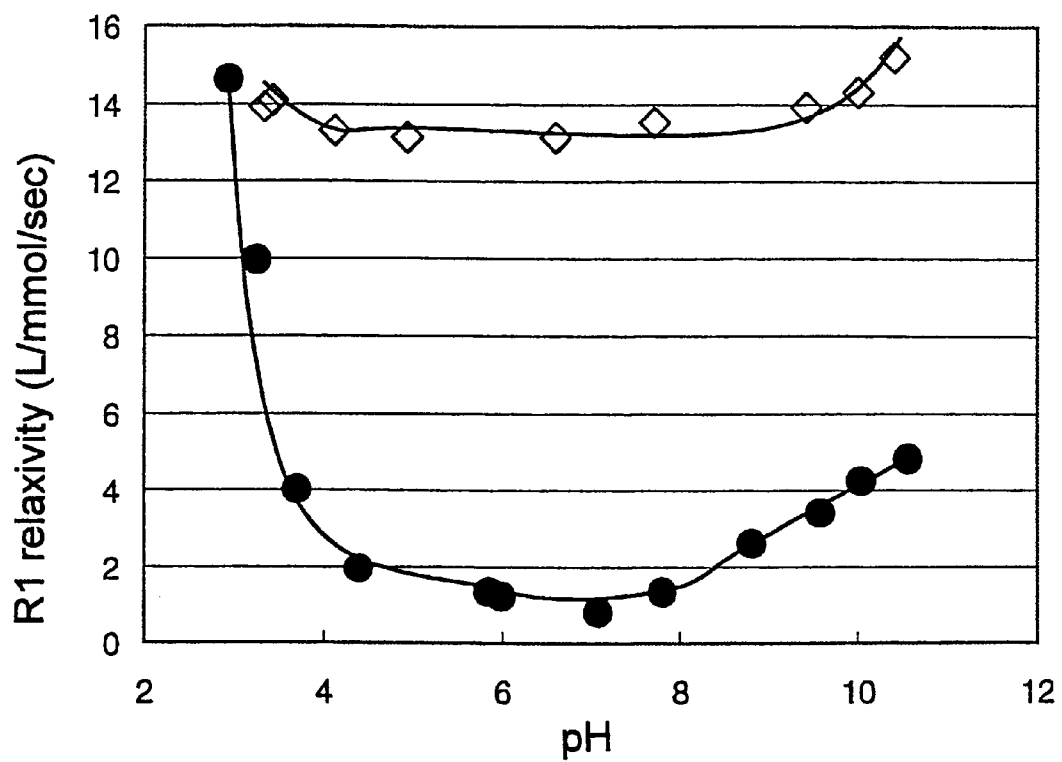
FIG. 7 shows the relationship between R1 relaxivity (calculated from T1 relaxing time) and changes in pH with respect to PLL(Gd-DTPA) (16%) or a mixture of PLL(Gd-DTPA) (16%) and PDEAMA, wherein -◇- shows PLL(Gd-DTPA) (16%) alone, and-●- shows a mixture of PLL(Gd-DTPA) (16%) and PDEAMA.

Relationship Between R1 Relaxivity and pH with Respect to Complex of PLL(Gd-DTPA) (16%) and PDEAMA With regard to the solution of [II] prepared in Example 13 (a), and a mixture solution of equal amounts of this solution of [II] and the solution of [II] prepared in Example 13 (b), pH of the solutions was adjusted to various values, and changes in proton relaxivity were examined. The proton relaxivity (reciprocal of T1 relaxing time, namely, R1 relaxivity) was measured according to Example 2. The results are shown in FIG. 7. The relaxivity of the mixture solution of the solution of [I] and the solution of [II] markedly decreased at pH 4 and became almost nil at around neutral. This means that at near neutral pH, the relaxivity of the mixture solution of the solution of [I] and the solution of [II] was at the same level with water, namely, was in the state that no relaxivity was exhibited. It is understood from this experiment that PLL(Gd-DTPA) (16%) and PDEAMA start to form a complex from about pH 4 and the imaging capability becomes almost completely off at a near neutral range.

Example 15

Relationship Between pH and MRI Signal Intensity with Respect to Complex of PLL(Gd-DTPA) (16%) and PDEAMA (a) Test method With regard to the solution of [I] prepared in Example 13 (a), and a mixture solution of equal amounts of this solution of [I] and the solution of [II] prepared in Example 13 (b), pH of the solutions was adjusted to various values and changes in MRI signal intensity were examined.

The [I] and the mixture of equal amounts of [I] and [II] were diluted with 80% v/v rabbit serum•0.15 M NaCl solution so that the final Gd concentration can be 1.0 mM, and pH was adjusted to 4, 5, 7 and 7.5 and used as test solutions. As a control solution, an 80% v/v rabbit serum•0.15 M NaCl solution was adjusted to pH 4, 5, 7 and 7.5 and used. The test solutions and control solutions at various pHs were charged respectively in 1 ml disposable syringes (5 mm$\phi$). The syringes were subjected to MRI imaging by using a 4.7T animal imager (Omega CSI-2, GE-Bruker). The MRI images were obtained by using synthesis of T1 and T2–WI (TR/TE=300/12 ms).

Figure 8:
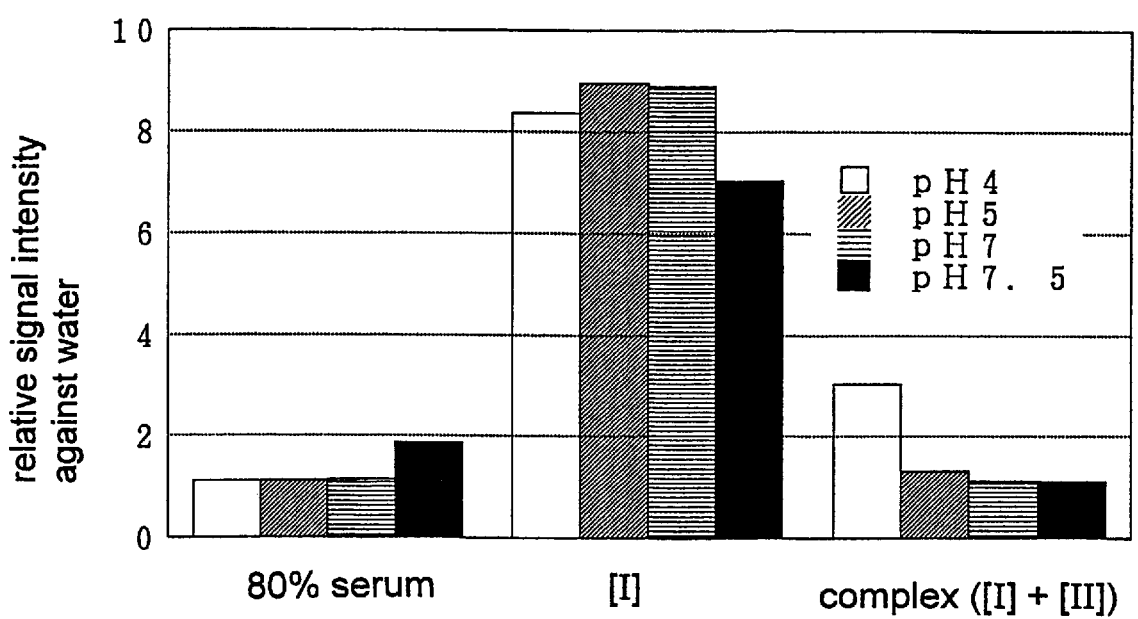
FIG. 8 shows the relationship between MRI signal intensity and pH with respect to PLL(Gd-DTPA) (16%) and a complex of PLL(Gd-DTPA) (16%) and PDEAMA, wherein □ shows the results at pH 4, ▨ shows the results at pH 5, ☰ shows the results at pH 7, and ■ shows the results at pH 7.5.

MRI signal intensities of the test solutions, the control solutions and water were determined, which were expressed as a relative intensity of test solutions or control solutions to water. The results are shown in FIG. 8.

(b) Results

MRI signal intensities of the mixtures of [I] and [II] at pH 5,7 and 7.5 are nearly the same as water (relative intensity being nearly1). In contrast, when the pH is 4, the relative intensity is approximately 3, and this means that imaging capability is exhibited. From these results, it is apparent that an MRI contrast medium containing a complex of [I] and [II] can successfully respond to changes in pH.

Experimental Example 1

Effect of Various Mixing Ratios of poly[Gd(DTPA-PDA)5]14 and PLH on T1 Relaxivity The T1 relaxivity at pH 6 and pH 7.5 (because the phase transit pH of PLH is about 6.5, pHs around 6.5 were examined) was determined, when the mixing ratios (weight ratios) of poly[Gd(DTPA-PDA)5]14 and PLH were changed.

The poly[Gd(DTPA-PDA)5]14 was dissolved in 15 mM phosphate buffers at pH 6 and pH 7.5 so that Gd concentration became 20 mM. The phosphate buffers had salt concentrations of 75 mM sodium chloride and 150 mM sodium chloride at pH 6, and of 150 mM sodium chloride at pH 7.5.

Figure 9:
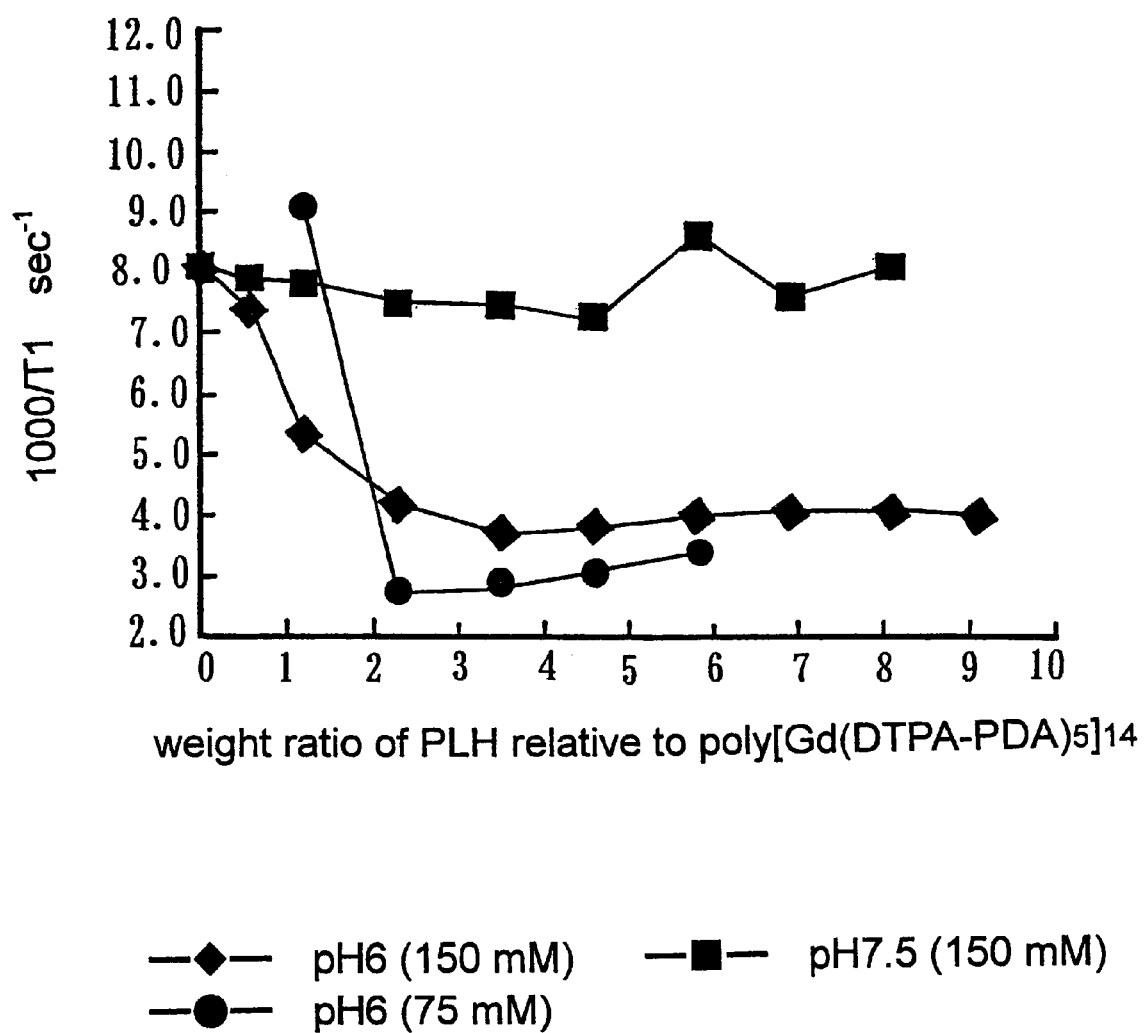
FIG. 9 shows the relationship between the amount of PLH in a complex of poly[Gd(DTPA-PDA)5]14 and PLH, and the reciprocal of T1 relaxing time, wherein -♦- shows the results at pH 6 (sodium chloride concentration: 150 mM),-●- shows the results at pH 6 (sodium chloride concentration: 75 mM), and -■- shows the results at pH 7.5 (sodium chloride concentration: 150 mM).

PLH was added to these solutions of poly[Gd(DTPA-PDA)5]14 (100 $\mu$l) in various weight ratios (poly[Gd (DTPA-PDA)5]14:PLH=1:0–9), and the final amount thereof was adjusted to 1 ml with the above-mentioned buffer (Gd concentration was 1 mM: 157 $\mu$g/ml). With respect to these sample solutions, T1 relaxing time was examined and the reciprocal thereof (relaxivity) was calculated in the same manner as in Example 2. The results are shown in FIG. 9. At pH 6, the T1 relaxivity decreased in every salt concentration solution having a weight ratio of the both ingredients of not less than about 1:2. The absence of changes in T1 relaxivity at pH 7.5 is considered to be attributable to the absence of a complex of PLH and poly [Gd(DTPA-PDA)5]14 at this pH.

Experimental Example 2

Determination of Gd Concentration of Various Mixtures of poly[Gd(DTPA-PDA)5]14 and PLH When the weight ratio of poly[Gd(DTPA-PDA)5]14 and PLH was changed in Experimental Example 1, T1 relaxivity changed at pH 6. Thus, the relationship was examined between the relaxivity and the Gd concentration of the test solution.

Figure 10:
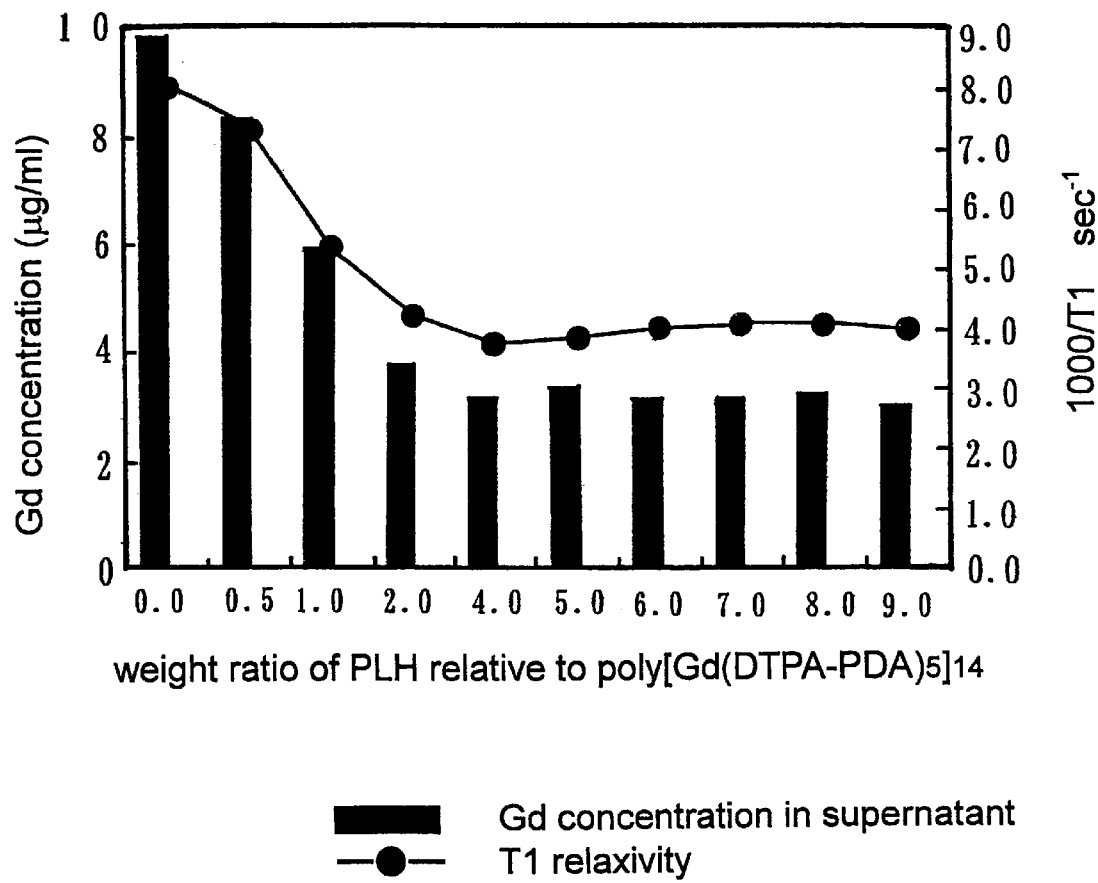
FIG. 10 shows the relationship between the amount of PLH in a complex of poly[Gd(DTPA-PDA)5]14 and PLH and the concentration of Gd in the supernatant of a sample of the complex, or the reciprocal of T1 relaxing time, wherein the bar graph shows concentration of Gd in the supernatant and the line graph shows the reciprocal of T1 relaxing time (relaxivity).

The poly[Gd(DTPA-PDA)5]14 was dissolved in 15 mM phosphate buffer (pH 6, salt concentration of 150 mM sodium chloride), so that the Gd concentration became 20 mM. PLH was added to said solution (100 $\mu$l) of poly[Gd-(DTPA-PDA)5]14 in various weight ratios (poly[Gd(DTPA-PDA)5]14:PLH=1:0–9), and the final amount thereof was adjusted to 1 ml with the above-mentioned buffer (Gd concentration was 1 mM: 157 $\mu$g/ml) and used as a sample solution. The above-mentioned complex solution was centrifuged at 12000 rpm for 5 min to separate supernatant and sediment. 0.3 ml of the obtained supernatant was diluted with 5 ml of water and subjected to determination of Gd concentration and T1 relaxivity. The T1 relaxivity was determined according to Example 2. The Gd concentration was determined by ICP (inductively coupled plasma, high frequency induction coupled plasma) at a determination wavelength of 342.247 nm, and at high frequency output of 1 KW (ICP emission spectroscopy, manufactured by Seiko Instruments Inc.). The relationship between the Gd concentration of the supernatant of each sample solution and T1 relaxivity is shown in FIG. 10. The T1 relaxivity was determined according to Example 2. The Gd concentration was determined by ICP (inductively coupled plasma, high frequency induction coupled plasma) at a determination wavelength of 342, 247 nm, and at high frequency output of 1 KW (ICP emission spectroscopy, manufactured by Seiko Instruments Inc.). The relationship between the Gd concentration of the supernatant of each sample solution and T1 relaxivity is shown in FIG. 10.

A fine correlation was found between the Gd concentration of each supernatant and T1 relaxivity, whereby it was confirmed that T1 relaxivity was dependent on the Gd concentration of the sample, namely, release of poly[Gd (DTPA-PDA)5]14 into the supernatant.

Experimental Example 3

MRI Signal Intensity of Contrast Medium Comprising a Complex of PLL(Gd-DTPA) (16%) and PDEAMA at Muscle and Tumor Tissues The response to pH in vivo of the contrast medium of the present invention was confirmed in this experimental example.

(a) Test Method

BALB/c nude mouse (ca. 20 g, female, 8 weeks of age) implanted with colon 26 adenocarcinoma cells, which were provided by Assistant Professor Mr. Susumu Nakajima of Asahikawa Medical University, was used as a test animal. [I] prepared in Example 13(a), and a mixture of equal amounts of said [I] and [II] prepared in Example 13 (b) were adjusted with 0.15 M NaCl (pH 7) so that the final Gd concentration can be 2.0 mM to obtain a contrast medium solution, then 100 $\mu$l of the contrast medium solution was injected directly into the tumor site and femoral muscle of this mouse. The MRI imaging and measurement of MRI signal intensity were conducted before injection, immediately after injection and 20 hours after injection under the same conditions as in Example 15. The MRI imaging and administration of each contrast medium were performed under anesthesia. The results are shown in FIG. 11.

Figure 11:
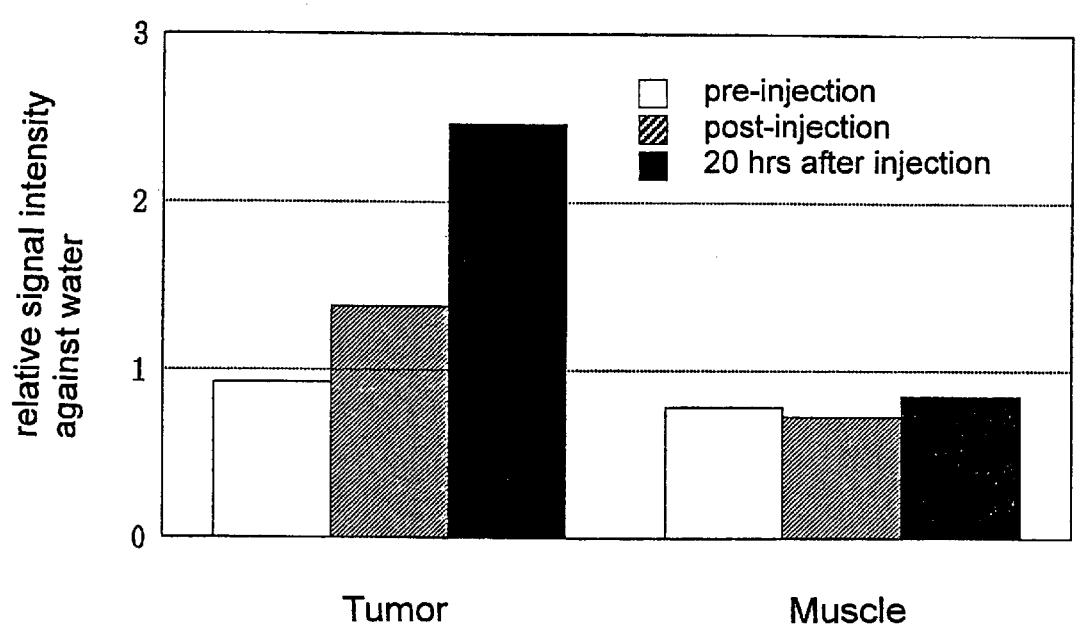
FIG. 11 shows variation in relative signal intensity due to the administration of the inventive MRI contrast medium to a tumor tissue and muscle, wherein □ shows the results before injection, ▨ shows the results immediately after injection and ■ shows the results at 20 hours after the injection.

As is evident from FIG. 11, MRI signal intensity at the normal muscle site showed no change even at 20 hours after the administration of the contrast medium and said site was not imaged. At tumor site, however, the signal intensity rose and the tumor tissue was specifically imaged with lapse of time.

The mechanism of tissue-specific imaging capability is postulated that the imaging capability of the contrast medium of the present invention became an on-condition with regard to pH response due to acidification on the cell surface by sugar chains of sialyl-Lewis acid and the like expressed on the cell surface of colon 26 cells. This result suggests advantageous application of the inventive MRI contrast medium for the imaging of inflammatory lesion similarly expressing sialyl-Lewis acid on the cell surface thereof.

Experimental Example 4

Figure 12:
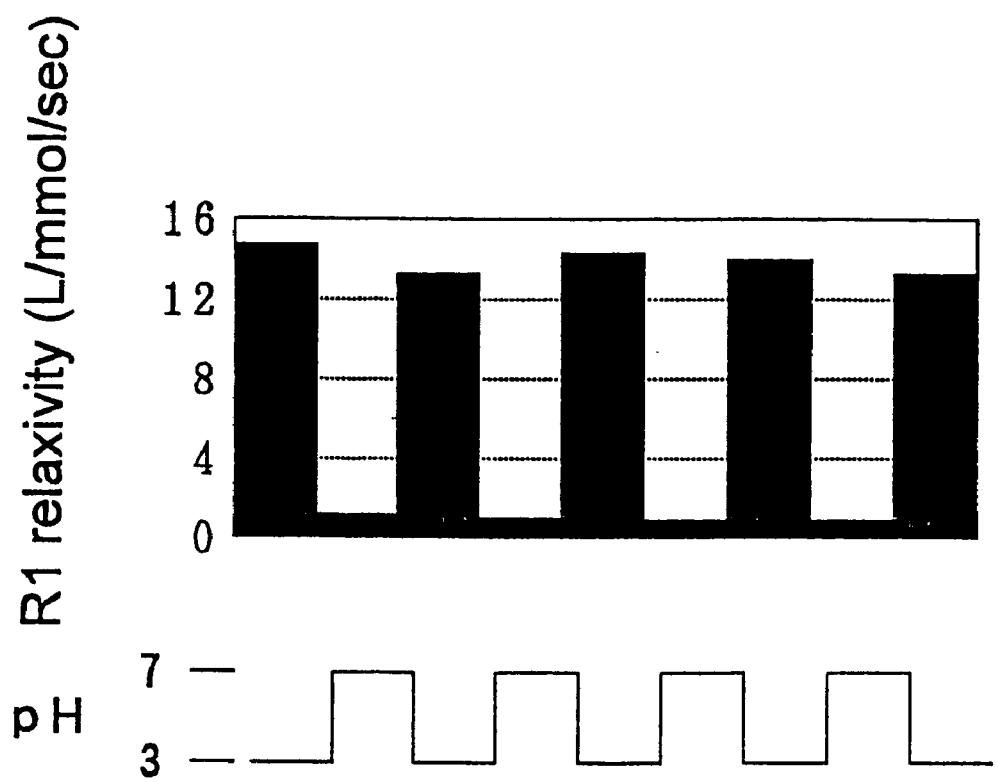
FIG. 12 is a graph showing the reversibility of the R1 of the inventive MRI contrast medium in response to pH.

Consideration on the Reversible Property of R1 Relaxivity of a Complex of PLL(Gd-DTPA) (16%) and PDEAMA (a) Preparation of Mother Liquor
(1) PLL(Gd-DTPA) (16%) mother liquor; prepared according to Example 13(a), 67.8 mg/ml•0.15 M NaCl
(2) PDEAMA mother liquor; prepared according to Example 13(b), 44.95 mg/ml•0.15 M NaCl
(b) Measurement Method The above-mentioned (1) (50 $\mu$l) and (2) (83 $\mu$l) and 0. 15 M NaCl were added and adjusted to 1 ml. To this sample were added 15 $\mu$l of 1N NaOH and 15 $\mu$l of 1N HCl to alternately change pH to about 3 and about 7. The R1 relaxivity was measured according to Example 2 using Minispec. The results are shown in FIG. 12.

(c) Results

The R1 value was about 14 at pH 3 and about 1 at pH 7, showing responses to pH. Therefore, the contrast medium of the present invention was confirmed to react to changes in pH and enable reversible on-off switching of MRI signal intensity.

Industrial Applicabilty

Due to the formation of a complex of a Gd type MRI contrast agent and a polymer material responsive to environmental changes, allowing on-off switching of imaging capability in response to changes in the environment, imaging does not occur in undesired parts, however, the imaging capability is expressed only in the target cells such as tumor. This consequently achieves drastic improvement in detection sensitivity at tumor and the like. Further, polymerization of said contrast medium leads to more superior imaging capability. An improved imaging capability enables MRI diagnosis with superior detection efficiency and less side effects.

This application is based on application No. 64497/1997 filed in Japan, the contents of which are incorporated hereinto by reference.

What is claimed is:

1. A MRI contrast medium comprising a polyion complex, formed by an ion interaction of a gadolinium (Gd) type contrast agent and a first polymer, wherein said first polymer undergoes a phase transition in response to environmental changes to develop a different water solubility.

2. The MRI contrast medium of claim 1, wherein said Gd type contrast agent is a polymerized contrast agent.

3. The MRI contrast medium of claim 2, wherein said polymerized contrast agent has a linear alternating copolymer structure.

4. The MRI contrast medium of claim 3, wherein said polymerized contrast agent is a complex polymer of Gd and poly(diethylenetriaminepentaacetic acid (DTPA)1,3-propanediamine (PDA)).

5. The MRI contrast medium of claim 1 or 2, wherein said environmental changes are changes in pH.

6. The MRI contrast medium of claim 5, wherein said first polymer is a member selected from the group consisting of a polydiethylaminoethylmethacrylate (PDEAMA), a poly L-histidine (PLH), a poly L-lysine (PLL), a poly(1-vinylimidazole) (PVI) and a derivative thereof; and wherein said derivative is said first polymer bonded to a hydrophilic synthetic polymer or polysaccharide by graft polymerization.

7. The MRI contrast medium of claim 1 or 2, wherein said environmental changes are changes in light.

8. The MRI contrast medium of claim 7, wherein said first polymer is poly[bis(4-dimethylamino)phenyl](4-vinylphenyl)-methyl-leucohydroxide or a derivative thereof, and wherein said derivative is said first polymer bonded to a hydrophilic synthetic polymer or polysaccharide by graft polymerization.

9. The MRI contrast medium of claim 1 or 2, wherein said environmental changes are changes in temperature.

10. The MRI contrast medium of claim 9, wherein said first polymer is poly(N-isopropylacrylamide) or a derivative thereof; and wherein said derivative is said first polymer bonded to a hydrophilic synthetic polymer or polysaccharide by graft polymerization.

11. The MRI contrast medium of claim 1 or 2, wherein said environmental changes are changes in expression or distribution of an enzyme in a living body.

12. The MRI contrast medium of claim 1, wherein said Gd type contrast agent is a polymer of a Gd complex and a second polymer which undergoes a phase transition in response to environmental changes to develop a different water solubility, and wherein said second polymer undergoes a phase transition in response to the same environmental changes as said first polymer to develop a different water solubility.

13. The MRI contrast medium of claim 12, wherein said environmental changes are changes in pH.

14. The MRI contrast medium of claim 13, wherein said second polymer in the Gd type contrast agent and said first polymer to be used to form a complex with said Gd type contrast agent are the same or different; wherein each of said first and said second polymer is a member selected from the group consisting of PDEAMA, PLH, PLL, PVI and a derivative thereof; and wherein said derivative is said first or second polymer bonded to a hydrophilic synthetic polymer or polysaccharide by graft polymerization.

15. The MRI contrast medium of claim 14, which does not provide imaging for a normal tissue but provides imaging for a tumor tissue and/or an inflammatory tissue.

16. The MRI contrast medium of claim 12, wherein said Gd type contrast agent is a polymer comprising poly L-lysine and Gd-DTPA.

17. The MRI contrast medium as claimed in any one of claim 1, 2 or 12, wherein said first polymer has been graft copolymerized to a synthetic polymer or polysaccharide.

18. The MRI contrast medium of claim 17, wherein said synthetic polymer is a hydrophilic polymer.

19. The MRI contrast medium of claim 1 or 12, providing imaging which is reversibly controlled in response to environmental changes.

20. A method for producing a contrast medium comprising a complex of a Gd type contrast agent and a first polymer, wherein said first polymer undergoes a phase transition in response to biological microenvironmental changes or environmental changes induced in a living body by physical stimulation from outside the body to develop a different water solubility, which comprises mixing or stirring said first polymer and said Gd type contrast agent in an aqueous solution having a pH of not more than a phase transition point of said first polymer.

21. An imaging method comprising:

administering a contrast medium comprising a complex of a Gd type contrast agent and a first polymer, wherein said first polymer undergoes a phase transition in response to biological microenvironmental changes or environmental changes induced in a living body by physical stimulation from outside the body to develop a different water solubility; and forming images by MRI.

22. The method of claim 20, wherein said Gd type contrast agent is a polymerized contrast agent.

23. The method of claim 20 or 22, wherein said environmental changes are changes in pH.

24. The method of claim 23, wherein said first polymer is a member selected from the group consisting of PDEAMA, PLH, PLL, PVI and a derivative thereof; and wherein said derivative is said first polymer bonded to a hydrophilic synthetic polymer or polysaccharide by graft polymerization.

25. The method of claim 20, wherein said Gd type contrast agent is a polymer of a Gd complex and a second polymer which undergoes a phase transition in response to environmental changes to develop a different water solubility, and wherein said second polymer undergoes a phase transition in response to the same environmental changes as said first polymer to develop a different water solubility.

26. The method of claim 25, wherein said environmental changes are changes in pH.

27. The method of claim 26, wherein said second polymer in the Gd type contrast agent and said first polymer which forms a complex with said Gd type contrast agent are the same or different; wherein each of said first and said second polymer is a member selected from the group consisting of PDEAMA, PLH, PLL, PVI and a derivative thereof; and wherein said derivative is said first or said second polymer bonded to a hydrophilic synthetic polymer or polysaccharide by graft polymerization.

28. The method of claim 21, wherein said Gd type contrast agent is a polymerized contrast agent.

29. The method of claim 21 or 28, wherein said environmental changes are changes in pH.

30. The method of claim 21, wherein said first polymer is a member selected from the group consisting of PDEAMA, PLH, PLL, PVI and a derivative thereof; and wherein said derivative is said first polymer bonded to a hydrophilic synthetic polymer or polysaccharide by graft polymerization.

31. The method of claim 21, wherein said Gd type contrast agent is a polymer of a Gd complex and a second polymer which undergoes a phase transition in response to environmental changes to develop a different water solubility; and wherein said second polymer undergoes a phase transition in response to the same environmental changes as said first polymer to develop a different water solubility.

32. The method of claim 31, wherein said environmental changes are changes in pH.

33. The method of claim 32, wherein said second polymer in the Gd type contrast agent and said first polymer to be used to form a complex with said Gd type contrast agent are the same or different; wherein each of said first and second polymer is a member selected from the group consisting of PDEAMA, PLH, PLL, PVI and a derivative thereof; and wherein said derivative is said first polymer bonded to a hydrophilic synthetic polymer or polysaccharide by graft polymerization.

34. The method of claim 33, which does not provide imaging for a normal tissue but provides imaging for a tumor tissue and/or an inflammatory tissue.

35. The method of claim 21 or 31, wherein said imaging can be reversibly controlled in response to environmental changes.

* * * * *